United States Patent [19]

Eckert et al.

[11] 4,230,702

[45] Oct. 28, 1980

[54] READILY ENTERALLY ABSORBABLE PHARMACEUTICAL COMPOSITIONS OF PER SE POORLY ENTERALLY ABSORBABLE PHARMACOLOGICALLY ACTIVE AGENTS

[75] Inventors: Theodor Eckert; Fritz H. Kemper, both of Muenster, Fed. Rep. of Germany

[73] Assignee: Kali-Chemie Pharma GmbH, Hanover, Fed. Rep. of Germany

[21] Appl. No.: 868,187

[22] Filed: Jan. 9, 1978

[51] Int. Cl.³ .................. A61K 31/56; A61K 31/34
[52] U.S. Cl. .................... 424/242; 424/182; 424/285; 536/7
[58] Field of Search .............. 536/7; 424/182, 242, 424/285

[56] References Cited

U.S. PATENT DOCUMENTS 3,514,441   5/1970   Satoh et al. .................. 536/7

FOREIGN PATENT DOCUMENTS 1432784   4/1976   United Kingdom .............. 424/312

*Primary Examiner*—Johnnie R. Brown
*Attorney, Agent, or Firm*—Schwartz, Jeffery, Schwaab, Mack, Blumenthal & Koch

[57] ABSTRACT

A readily enterally absorbable pharmaceutical composition of pharmacologically active agents, which per se are poorly enterally absorbable, is disclosed which comprises a pharmacologically, effective amount of at least one such pharmacologically active agent distributed in a vehicle comprising an absorption-enhancing amount of at least one partial glyceride of a fatty acid of long chain length. The preparation is suited for formulating cardiac glycosides, steroids, or anti-capillary fragility agents.

18 Claims, No Drawings

1

READILY ENTERALLY ABSORBABLE PHARMACEUTICAL COMPOSITIONS OF PER SE POORLY ENTERALLY ABSORBABLE PHARMACOLOGICALLY ACTIVE AGENTS

BACKGROUND OF THE INVENTION

The present invention relates to readily absorbable enteral pharmaceutical formulations of pharmacologically active agents which are poorly absorbable per se, and to a method for preparing such formulations.

It is well known in the art that a number of pharmacologically active agents are absorbed in the gastrointestinal tract only to a low and unpredictable percent, or not at all. For some pharmacologically active agents, the poor enteral absorbability may be due to their insufficient solubility in water. Yet, pharmacologically active agents which are not satisfactorily enterally absorbable are also found amongst water soluble pharmacologically active agents.

In some cases, the absorbability of such unsufficiently enterally absorbable pharmacologically active ingredients can be improved by means of a technological treatment of the pharmacologically active agent, e.g., by means of micronization, formation of an adsorbate or adduct or addition of dissolving additives. Yet, the enterally applied dosage which is necessary to achieve a desired pharmacological effect, nearly always is substantially higher than the amount of the pharmacologically active agent which would be required in the case of a complete bioavailibility of this agent.

Yet, there is a need for pharmaceutical formulations which provide such per se poorly enterally absorbable pharmacologically active agents not only in an injectable formulation, but also in orally and/or rectally applyable formulations which provide a high degree of enteral absorption of these pharmacologically active agents.

SUMMARY OF THE INVENTION

It is an object of the present invention to provide an enteral pharmaceutical formulation of pharmacologically active agents which per se are poorly absorbable, which provide for a high degree of enteral absorption of such pharmacologically active agents.

It is a further object of the present invention to provide such a formulation wherein the enteral absorption of the per se poorly enterally absorbable pharmacologically active agents is increased sufficiently to permit an enteral application of these pharmacologically active agents.

It is a special object of the present invention to provide such a formulation of a per se poorly enterally absorbable cardiac glycosides, in particular of g-strophanthin, k-strophanthin, or proscillaridin, preferably such a formulation wherein the enteral absorption of poorly absorbable cardiac glycosides is sufficiently high to insure a constant degree of absorption of such glycosides after enteral application.

It is a further special object of the present invention to provide such a formulation of per se poorly enterally absorbable steroids, e.g., steroid hormones and derivatives thereof, in particular pregn-4-ene-3,20-diones and pregna-4,6-diene-3,20-diones, such as progesterone, medrogestone and similar gestagenes.

It is a further object of the present invention to provide such a formulation of per se poorly enterally absorbable agents which are effective in treating and preventing impaired capillary strength, in particular benzofuran derivatives such as benzarone.

In order to accomplish the foregoing objects and advantages of the present invention, there is provided a readily absorbable pharmaceutical composition which comprises a pharmacologically-effective amount of at least one per se poorly enterally absorbable pharmacologically active agent distributed in a vehicle comprising an absorption enhancing amount of at least one partial glyceride of a fatty acid of long chain length.

The pharmacologically active agent may be incorporated in the partial glyceride or a mixture of partial glycerides, respectively, in form of a genuine solution, a solid solution, or a microcrystalline suspension.

The preparation according to the present invention is preferably suited for formulating per se poorly enterally absorbable cardiac glycosides, in particular k-strophanthin, g-strophanthin, and proscillaridin, per se poorly enterally absorbable steroids, in particular pregn-4-ene-3,20-diones and pregna-4,6-diene-3,20-diones, preferably gestagenes, most preferably progesterone, medrogestone, and per se poorly enterally absorbable agents which are effective in preventing or treating impaired capillary strength, in particular benzofuran derivatives, preferably benzofuran derivatives which are described in the U.S. Pat. No. 3,012,042, the disclosure of which is hereby incorporated by reference, most preferably 2-ethyl-3-(4-hydroxybenzoyl)benzofuran, which is known in the medical art under the generic name benzarone.

According to the present invention, there is further provided a process for preparing a readily enterally absorbable pharmaceutical composition of per se poorly enterally absorbable pharmacologically active agents which comprises the step of dissolving these agents in at least one partial glyceride of a fatty acid of long chain length.

According to the present invention, there is further provided a method of enteral medication which comprises enterally, preferably orally, administering the above described pharmaceutical composition to a larger mammal.

DETAILED DESCRIPTION OF PREFERRED EMBODIMENTS

It has been found that dissolving or suspending per se poorly enterally absorbable pharmacologically active agents, in partial glycerides of fatty acids of long chain length, leads to a useful and satisfactory increase of the enteral absorption of such agents.

Partial glycerides of fatty acids of long chain length possess excellent dissolving properties for dissolving hydrophilic as well as lypophilic substances and therefore are particularly suitable vehicles for per se poorly enterally absorbable pharmacologically active agents.

Partial glycerides of fatty acids of long chain length comprise mono-and diglycerides of saturated and/or unsaturated fatty acids, having a chain length of preferably between about 12 to about 18, most preferably between about 14 and about 18 carbon atoms, and mixtures thereof. Especially suited are mono-and diglycerides of oleic, palmitic, and stearic acids and mixtures thereof.

The term "pharmacologically active agent" as used in the present specification and claims is meant to connote agents which are effective in larger mammals, in particular human beings, in treating or preventing diseases and/or disorders in the body functions and/or influencing the state of the body and its functions in a desirable manner. The term "per se poorly enterally absorbable" as used in the present specification and claims is meant to connote such agents, which upon being enterally applied in a solid or liquid formulation devoid of any dissolution and/or absorbability improving additives exhibit such a low and/or slow per se enteral absorbability, that by means of enteral administration, a pharmacologically effective level in the body of larger mammals cannot be reached or can be reached only by an administering enteral dosages which correspond to at least 2 times the parenterally effective dosage of the respective agent, or that only less than 50% of the enteral dosage which is necessary to achieve a pharmacologically effective level of the respective agent in the body are actually absorbed in the gastrointestinal tract.

Whether the actual per se enteral absorbability of a respective pharmacologically active agent is sufficient or insufficient, of course, will depend largely on the chemical and physical properties of said agent, especially the kind and degree of its pharmacological activity as well as the desired pharmacological effect.

Preparations according to the present invention are suited for the enteral application of cardiac glycosides which per se are particularly poorly enterally absorbable, for example, cardiac glycosides of which only about 5% or less, e.g., between about 5 and 0.3% are enterally absorbed.

Because of their favorable effect on the force of the myocardial contraction, cardiac glycosides are used therapeutically as cardiotonics for the treatment of myocardial insufficiency and congestive heart failure.

The term "cardiac glycosides", as it is used in the present application, includes cardiotonically-active glycosides containing a cardenolid- or bufadienolid aglycon, which is substituted in the 3-position by a glycosidic group containing 1 to 4 sugar units, and semi-synthetical derivatives thereof. The sugar units may be pentose or hexose units or partial products thereof.

Cardiontonically-active semi-synthetic derivatives of naturally-occuring cardiac glycosides include the aglycones themselves, glycosides wherein the original number of sugar units is reduced, glycosides wherein the glycosidic group and/or the aglycon are chemically modified by etherification or esterification of at least part of the hydroxy groups with lower alkyl or lower carboxylic acyl, hydroxylation or dehydrogenation.

Among the cardiac glycosides with cardenolid structure, there may be cited the digitalis glycosides which occur naturally in digitalis purpurea and digitalis lanata, and derivatives thereof, e.g., lanatosids A, B or C, purpurea glycosides A or B, digitoxin, digoxin or gitoxin or in the aglycons thereof, k-strophanthus glycosides which occur naturally in strophanthus kombe, g-strophanthus glycosides which occur naturally in strophanthus gratus, e.g., k-strophanthins, $\alpha$, $\beta$, and $\gamma$ containing the aglycon k-strophanthidin ($=3\beta$, 5,14-trihydroxy-19-oxo-5$\beta$-card-20(22)-enolid) and g-strophanthin containing the aglycon g-strophanthidin ($=1\beta$, 3$\beta$, 5,11$\alpha$, 14,19-hexahydro-5$\beta$-card-20(22)-enolid).

Among the cardiac glycosides with bufadienolid structures, there may be cited the squill glycosides which occur naturally in scilla martima, e.g., proscillaridin scillaren A, scillaren B.

Examples of per se poorly enterally absorbable cardiac glycosides are g-strophanthin, k-strophanthin and proscillaridin. Preparations according to the present invention are also suited for the enteral application of cardiac glycosides for which it is desirable to improve their enteral absorption.

The concentration of the cardiac glycoside in the enteral preparations according to the present invention may vary considerably depending on the physical and chemical properties, especially the pharmacological activity or the respective cardiac glycoside which is used, on its enteral absorbability per se, and on its sensitivity to metabolic decomposition in the gastrointestinal tract and/or the liver, as well as on the amount of absorption enhancing partial glycerides present in the preparation and the contemplated mode of administration, the treated condition and the therapy which is desired. Usually a satisfactory enteral activity is obtained with an amount corresponding to between about 1 and about 3 times, preferably about 1 and about 2 times the parenterally-effective amount of the respective cardiac glycosides. For example, enterally-effective amounts of g-strophanthin, k-strophanthin or proscillaridin within the compositions according to the present invention are between about 0.1 and about 0.3, preferably about 0.2 and 0.25 mg per single dosage unit.

Preparations according to the present invention are also suited for the enteral application of steroids which per se are particularly poorly enterally absorbable.

The term "steroids" as it is applied in the present application includes steroid hormones, in particular gestagene hormones, and synthetic and semi-synthetic derivatives thereof, especially pregn-4-ene-3,20-diones and pregna-4,6-diene-3,20-diones. Examples of per se poorly enterally absorbable steroids are progesterone and medrogestone.

The pharmacological properties of the steroids and the medical application thereof are well known in the art.

The concentration of the steroid in the enteral preparations according to the present invention may vary considerably depending on the physical and chemical properties, especially the pharmacological activity of the respective steroid which is used, on its enteral absorbability per se, and on its sensitivity to metabolic decomposition in the gastrointestinal tract and/or the liver, as well as on the amount of absorption enhancing partial glycerides present in the preparation and the contemplated mode of administration, the treated condition and the pharmacological effect which is desired. Usually a satisfactory enteral activity is obtained with an amount corresponding to between about 1 and about 3 times, preferably about 1 and about 2 times the parenterally effective amount of the respective steroid. For example, enterally-effective amounts of progesterone or medrogestone within the compositions according to the present invention are between about 2 and about 50 mg per single dosage unit.

Preparations according to the present invention are also suited for the enteral application of agents which are effective in improving the capillary strength and which per se are particularly poorly enterally absorbable.

Agents which are effective in improving the capillary strength are useful in preventing or treating impaired capillary strength, especially in veins, and/or in preventing or treating abnormal capillary permeability and/or capillary fragility.

Examples of per se poorly enterally absorbable agents are benzofuran derivatives in particular benzarone.

The concentration of such agents in the enteral preparations according to the present invention may vary considerably depending on the physical and chemical properties, especially the pharmacological activity of the respective agent which is used, on its enteral absorbability per se, and on its sensitivity to metabolic decomposition in the gastrointestinal tract and/or the liver, as well as on the amount of absorption enhancing partial glycerides present in the preparation and the contemplated mode of administration, the treated condition and the therapy which is desired. For example, enterally-effective amounts of benzarone within the compositions according to the present invention are between about 25 and about 100 mg per single dosage unit.

The amount of absorption enhancing partial glycerides of fatty acids of long chain length in the preparation according to the present invention, which is effective to sufficiently enhance the enteral absorption to permit an enteral administration of the per se poorly enterally absorbable pharmacologically active agent, may vary considerably depending on the per se enteral absorbability of the respective agent, as well as on the chemical and physical properties of any other ingredients of the composition. Typically, satisfactory results are obtained with preparations wherein the amount of partial glycerides of fatty acids of long chain length are between about 20 and about 100%, preferably about 40 and about 100% of the vehicle. For example, in oral preparations of cardiac glycosides the per se enteral absorbability of which is less than 5%, e.g., between 0.3 and 5%, such as g-strophanthin, k-strophanthin or proscillaridin, the partial glycerides of fatty acids of long chain length are preferably used in amounts of about 40 to about 100% of the total vehicle.

In oral preparations of per se poorly enterally absorbable steroids, such as progesterone or medrogestone, the partial glycerides of fatty acids of long chain length are preferably used in amounts of about 40 to about 100% of the total vehicle.

In oral preparations of the capillary strength improving agents, such as benzarone, the partial glycerides of fatty acids of long chain length are preferably used in amounts of about 40 to about 100% of the total vehicle.

The ratio between the amounts of the per se poorly enterally absorbable pharmacologically active agent and of absorption enhancing partial glycerides of fatty acids of long chain length may vary considerably depending on the per se enteral absorbability of the respective agent, as well as on the chemical and physical properties of any other ingredients of the composition. For example, for enteral preparations of cardiac glycosides having a per se enteral absorbability of less than 5%, e.g., of between 0.3 and 5%, a suitable ratio cardiac glycoside/partial glyceride of fatty acids of long chain length is of between about 0.5 to 100 and about 0.01 to 100.

For the enteral preparations of per se poorly enterally absorbable steroids such as progesterone or medrogestone a suitable ratio steroid/partial glyceride of fatty acids of long chain length is of between about 5 to 100 and about 0.5 to 100.

For enteral preparations of per se poorly enterally absorbable, the capillary strength improving agents such as benzarone, the respective ratio suitably is between about 10 to 100 and about 1 to 100.

The enteral formulations may take the form of solid or liquid formulations for oral or rectal application. Thus, the formulations may be in the form of capsules, tablets, coated tablets, suppositories or emulsions. These formulations can easily be prepared according to the present invention, since the partial glycerides which are utilized according to the present invention comprise partial glycerides which at room temperature are liquid as well as such partial glycerides which at room temperature are solid. By mixing the appropriate partial glycerides, nearly any desired consistency can be obtained and/or a melting point which is suitable for rectally applied suppositories can be achieved.

If desired, these formulations may further comprise conventional pharmaceutical carriers and additives, for example, viscosity-improving and/or structure- or matrix-forming additives which provide for an appropriate viscosity and physical structure. Suitable such additives are, e.g., inorganic or organic thickening and structure-forming agents such as, saturated higher fatty acids and alcohols containing, e.g., 12 to 20 carbon atoms, for example, stearic or palmitic acid, stearic or cetylic alcohol, waxes like beeswax, synthetic esters of higher fatty acids and higher fatty alcohols, or partial glycerides of fatty polyhydroxy acids (e.g., the commercial products "Softigen 701"). Suppositories may further contain any conventional water soluble or fatty suppository bases as additional vehicles. The compositions may further comprise pharmaceutical adjuvants, e.g., binders or lubricants for tabletting, stabilizing-, flavoring-, or emulsifying agents or preservatives.

If the pharmacologically active ingredients within the composition are sensitive to acids, it may be advisable to apply an enteric coating to the oral dosage forms, e.g., gelatin capsules, of such agents.

The formulations according to the present invention are prepared in any conventional manner, e.g., by dissolving the per se poorly enterally absorbable pharmacologically active agents in the partial glycerides, optionally adding additional adjuvants, and formulating the resulting mixture into the desired dosage form by known pharmaceutical methods, e. g., tabletting, molding into suppositories or filling into capsules.

Depending on the solubility and/or the dissolution rate of the pharmacologically active agent in the partial glycerides and on the melting point of the partial glycerides, the dissolving may be done at room temperature or under heating. In cases where these pharmacologically active agents recrystallize and/or the partial glycerides resolidify upon cooling of such solutions which are obtained under heating, microcrystalline suspensions and/or solid solutions of these agents are formed, which exhibit the same absorption behavior as that of actual solutions of these pharmacologically active agents.

In order to facilitate the filling of the mixture into gelatin capsules or the formulating into suppositories or tablets, it may be advisable to further add conventional pharmaceutical additives.

The high enteral absorption of the formulations according to the present invention is demonstrated by toxicity tests, determination of the level of the respective pharmacological agents in the blood or determination of the amount of the pharmacologically active agent which is excreted through the kidneys.

For testing the toxicity, solutions of g-strophanthin, proscillaridin A or medrogestone in various mixtures of mono-and diglycerides of long chain fatty acids and comparative formulations of the same pharmacologically active agents suspended in a tylose solution in water are administered orally to female guinea pigs of 250 to 300 g body weight by means of an oral feeding tube. The lethal doses which are observed in the various formulations are given in Table I below.

The data in Table I demonstrate the improved enteral absorbability of the pharmacologically active agents which are dissolved in the partial glycerides.

Table I

| pharmacologically active agent | $LD_{50}$ (mg/kg) | | | |
|---|---|---|---|---|
| | in Tylose[1] | in Witafrol 7470[2] | in Peceol[3] | in Rilanit GMO[4] |
| g-strophanthin | 34.8 | 8.28 | 8.38 | — |
| proscillaridin A | 12.3 | 6.81 | 7.77 | — |
| medrogestone | 1470 | — | 850 | 862 |

[1] methylcellulose, manufacturer Farbwerke Hoechst AG
[2] mixture of mono-, and diglycerides of oleic acid comprising about 40% of monoester and about 60% of diester, manufacturer Dynamit Nobel AG
[3] mixture of mono-, di-, and triglycerides of oleic acid comprising about 30% of monoester, manufacturer Etablissement Gattefosse SFPA
[4] mixture of mono-, and diglycerides of oleic acid comprising about 40% of monoester and 60% of diester, manufacturer Henkel & Cie GmbH For determining the blood level values, a dose of 1000 mg/kg of benzarone in form of a solution in Rilanit GMO[4]) and in form of a suspension in water are administered to rats by means of an oral feeding tube.

Subsequently every two hours including the 10th hour, 8 animals of each group, and after 15 hours, 4 more animals of each group are sacrificed and their blood is recovered by means of a cordial cut. The amount of benzarone in the serum is determined spectrophotometrically. The measured blood level values are plotted on a graph and the areas beneath the resulting blood level curves are compared. From the comparison of the areas, an increase of the concentration of benzarone in the serum of 257% is calculated for the solution of benzarone in Rilanit GMO[4]) as compared with the concentration which is achieved with the aqueous benzarone suspension.

For determining the renal excretion, a dose of 20 mg/kg of carbon-14 labelled progesterone in the form of solutions in various mixtures of partial glycerides of long chain fatty acids and a comparative formulation wherein the progesterone is suspended in an aqueous tylose solution are administered orally to female guinea pigs having an average body weight of about 300 g. The urine of the animals is collected every 24 hours and the $^{14}C$-content in equal amounts of the urine is determined. The cumulated amount of excreted material is shown in Table II below in % of the administered dose. The percentage of excreted material is about 83% for the solution of progesterone in Peceol. This amount is about twice as high as that obtained from the suspension of progesterone in the tylose solution.

Furthermore doses of 1000 mg/kg of benzarone in the form of a solution in Rilanit GMO[4]) and in form of a suspension in water are orally administered to rats by means of an oral feeding tube. The urine of the animals is collected every 2 hours over a period of 15 hours and the amount of the excreted benzarone therein is determined spectrophotometrically. The measured values are plotted on a graph and the areas beneath the resulting curves are compared. From the comparison of the areas an increase of the renal excretion of benzarone of 437% is calculated for the solution of benzarone in Rilanit GMO[4]) as compared with that obtained from the aqueous benzarone suspension.

The invention will now be further described by the following examples. In these examples, the term "parts" means "parts by weight" unless stated otherwise.

TABLE II

Cumulative Renal Excretion of Progesterone in % of the Administered Dose

| vehicle time | Tylose | Tegin O[5] | Tegomuls X10[6] | Tegomuls X17[7] | Peceol X1[8] | Softigen 701[9] |
|---|---|---|---|---|---|---|
| 1. day | 29.7 | 37.9 | 42.5 | 43.7 | 46.0 | 51.6 |
| 2. day | 39.1 | 48.7 | 58.3 | 55.0 | 64.6 | 63.2 |
| 3. day | 43.0 | 51.6 | 69.2 | 62.0 | 71.6 | 66.2 |
| 4. day | 44.0 | 52.3 | 75.2 | 66.6 | 76.1 | 66.9 |
| 5. day | 44.5 | 52.6 | 78.8 | 70.0 | 79.1 | 67.4 |
| 6. day | 46.2 | 52.8 | 80.6 | 71.9 | 81.1 | 67.6 |
| 7. day | 46.4 | 52.9 | 81.9 | 73.9 | 82.9 | 67.7 |

[5] mixture of mono-, and diglycerides of oleic acid comprising about 60% of mono- and 40% of diester, manufactuer T.H. Goldschmidt AG
[6] mixture of 50 parts by weight of Tegomuls SO and 10 parts by weight of Rilanit GDO; Tegomuls SO is a partially hydrolized soy oil, comprising about 35-40% of monoglyceride, manufacturer T.H. Goldschmidt AG; Rilanit GDO is a partial glyceride of oleic acid, comprising about 20% of monoester and 50% of diester, manufacturer Henkel & Cie GmbH
[7] mixture of 45 parts by weight of Tegomuls SO, 45 parts by weight of Tegomuls SB and 10 parts by weight of Miglyol 812; Tegomuls SB is a partially hydrolized sunflower oil, comprising about 60% of monoglyceride, manufacturer T.H. Goldschmidt AG; Miglyol 812 is a mixture of triglycerides of medium chain length fatty acids, manufacturer Dynamit Nobel AG
[8] mixture of 50 parts by weight of Peceol and 10 parts by weight of Rilanit GDO
[9] mixture of partial glycerides of an unsaturated fatty acid which is rich in hydroxy groups, manufacturer Dynamit Nobel AG

EXAMPLE 1

Gelatin Capsules

Composition of the mixture which is filled in the capsules:

| Progesterone | 10 parts |
|---|---|
| Tegomuls SO | 400 parts |
| Rilanit GDO | 90 parts |
| Total | 500 parts |

Preparation:

The progesterone is dissolved at 40°, while stirring, in a mixture of Tegomuls SO (manufacturer T. H. Goldschmidt AG) and Rilanit GDO (manufacturer Henkel & Cie GmbH). Portions of 500 mg each of this solution are filled into a gelatin capsule, so that each capsule contains 10 mg of progesterone.

EXAMPLE 2

Gelatin Capsules

| Progesterone | 10 parts |
|---|---|
| Peceol | 400 parts |
| Rilanit GDO | 90 parts |
| Total | 500 parts |

Preparation:

The progesterone is dissolved at 40°, while stirring, in a mixture of Peceol (manufacturer Etablissement Gattefossé SFPA, Lyon) and Rilanit GDO (manufacturer Henkel & Cie GmbH). Portions of 500 mg each of this solution are filled into a gelatin capsule, so that each capsule contains 10 mg of progesterone.

EXAMPLE 3

Gelatin Capsules

| Benzarone | 100 parts |
|---|---|
| Rilanit GMO | 900 parts |
| Total | 1000 parts |

Preparation:

Benzarone is dissolved in Rilanit GMO (manufacturer Henkel & Cie GmbH) which is liquefied at 60°. Portions of 1000 mg each of this solution are filled into a gelatin capsule, so that each capsule contains 100 mg of benzarone.

EXAMPLE 4

Gelatin Capsules

| | |
|---|---|
| g-Strophanthin | 0.25 parts |
| Witafrol 7470 | 199.75 parts |
| Total | 200 parts |

Preparation:

g-Strophanthin is dissolved at 40°, while stirring, in Witafrol 7470 (manufacturer Dynamit Nobel AG). Portions of 200 mg of this solution are filled into a gelatin capsule, so that each capsule contains 0.25 mg of g-Strophanthin.

EXAMPLE 5

Gelatin Capsules

| | |
|---|---|
| Proscillaridin A | 0.1 parts |
| Witafrol 7470 | 99.9 parts |
| Total | 100 parts |

Preparation:

Proscillaridin A is dissolved at 40°, while stirring, in Witafrol 7470 (manufacturer Dynamit Nobel AG). Portions of 100 mg of this solution are filled into a gelatin capsule, so that each capsule contains 0.1 mg of Proscillaridin A.

EXAMPLE 6

Rectal Capsule

| | |
|---|---|
| Benzarone | 100 parts |
| Softigen 701 | 1300 parts |
| Tegin O | 600 parts |
| Total | 2000 parts |

Preparation:

Benzarone is dissolved at 50° in a molten mixture of Softigen 701 and Tegin O. After cooling the solution, portions of 2000 mg each are filled into a rectal capsule, so that each capsule contains 100 mg of benzarone.

EXAMPLE 7

Gelatin Capsules

| | |
|---|---|
| Medrogestone | 25 parts |
| Rilanit GMO | 475 parts |
| Total | 500 parts |

Preparation:

Medrogestone is dissolved, while stirring, in Rilanit GMO, (manufacturer Henkel & Cie GmbH), which is melted at 55°. After cooling of the mixture, portions of 500 mg each are filled into a gelatin capsule, so that each capsule contains 25 mg of medrogestone.

EXAMPLE 8

Gelatin Capsules

| | |
|---|---|
| Medrogestone | 25 parts |
| Peceol | 475 parts |
| Total | 500 parts |

Preparation:

Medrogestone is dissolved, while stirring, in Peceol, (manufacturer Etablissement Gattefosse SFPA), which is meted at 55°. After cooling of the mixture, portions of 500 mg each are filled into a gelatin capsule, so that each capsule contains 25 mg of medrogestone.

What is claimed is:

1. A readily enterally absorbable pharmaceutical composition of a per se poorly enterally absorbable pharmacologically-active agent selected from the group consisting of (1) a steroid selected from the group consisting of pregn-4-ene-3,20-dione or a pregna-4,6-diene-3,20-dione, gestagen and medrogestone and (2) an agent which is effective in improving the capillary strength comprising 2-ethyl-3-(4-hydroxybenzoyl) benzofuran, which comprises a pharmacologically effective amount of the pharmacologically-active agent distributed in a vehicle comprising an absorption enhancing amount of a glyceride selected from the group consisting of monoglycerides and diglycerides of oleic acid, stearic acid and palmitic acid and mixtures thereof.

2. The composition as defined in claim 1, which comprises a solution of the per se poorly enterally absorbable pharmacologically active agent in the glyceride.

3. The composition as defined in claim 1, which comprises a microcrystalline suspension of the per se poorly enterally absorbable pharmacologically active agent in the glyceride.

4. The composition as defined in claim 1, wherein the per se poorly enterally absorbable pharmacologically active agent comprises one of said steroids.

5. The composition as defined in claim 4, wherein the steroid is a pregn-4-ene-3,20-dione or a pregna-4,6-diene-3, 20-dione.

6. The composition as defined in claim 4, wherein the steroid is a gestagen.

7. The composition as defined in claim 4, wherein the steroid is progesterone.

8. The composition as defined in claim 4, wherein the amount of the steroid per single dosage unit is about 1 to about 2 times the parenterally-effective amount of the respective steroid.

9. The composition as defined in claim 6, wherein the amount of the steroid per single dosage unit is between about 2 and 50 mg.

10. The composition as defined in claim 1, wherein the per se poorly enterally absorbable pharmacologically active agent comprises 2-ethyl-3-(4-hydroxybenzoyl) benzofuran.

11. The composition as defined in claim 10, wherein the amount of the active agent per single dosage unit is between about 25 and 100 mg.

12. The composition as defined in claim 1, wherein the amount of glycerides is between about 20 and about 100% by weight of the vehicle.

13. The composition as defined in claim 12, wherein the amount of the glycerides is from about 40 to about 100% by weight of the vehicle.

14. The composition as defined in claim 4, wherein the per weight ratio steroid/glyceride is of between about 5 to 100 and 0.5 to 100.

15. The composition as defined in claim 10, wherein the per weight ratio active agent/glyceride is of between about 10 to 100 and 1 to 100.

16. A method of capillary strengthening treatment which comprises enterally administering to a human being a pharmaceutical composition as defined in claim 10.

17. A method of treatment of steroid hormone deficiencies which comprises enterally administering to a human being a pharmaceutical composition as defined in claim 4.

18. The composition as defined in claim 4, wherein the steroid is medrogestone.

* * * * *